(12) United States Patent
Nakayasu et al.

(10) Patent No.: US 7,459,587 B2
(45) Date of Patent: Dec. 2, 2008

(54) PROCESS FOR PURIFYING MENTHOL

(75) Inventors: Hidetoshi Nakayasu, Shizuoka (JP);
Yasuhiro Mizuno, Shizuoka (JP);
Hideyuki Hongo, Shizuoka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 12/076,153

(22) Filed: Mar. 14, 2008

(65) Prior Publication Data

US 2008/0228013 A1    Sep. 18, 2008

(30) Foreign Application Priority Data

Mar. 16, 2007 (JP) ............................. 2007-069210

(51) Int. Cl.
*C07C 35/12* (2006.01)
*C12P 7/00* (2006.01)

(52) U.S. Cl. ..................................... 568/829

(58) Field of Classification Search ................ 568/829; 435/132
See application file for complete search history.

(56) References Cited

U.S. PATENT DOCUMENTS 394,181 A    12/1888    Hindhaugh, Jr.

FOREIGN PATENT DOCUMENTS

| JP | 4-260401 | 9/1992 |
|----|----------|--------|
| JP | 9-217084 | 8/1997 |

*Primary Examiner*—Jafar Parsa
(74) *Attorney, Agent, or Firm*—McDermott Will & Emery LLP

(57) ABSTRACT

Crude menthol is dissolved in nitrile series solvent and then menthol is precipitated by cooling the solution to thereby obtain optically and chemically substantially pure menthol, the enantiomeric excess thereof being more than about 99% e.e. and the chemical purity being more than about 99%. Preferred examples of the nitrile series solvent include acetonitrile and propionitrile. The dissolution of crude menthol is carried out at a temperature below 42° C., which is the melting point of menthol. The cooling temperature in crystallization is preferably at a room temperature or a little lower temperature than the room temperature. After crystallization of menthol, additional purification process such as a distillation may be conducted, if necessary.

3 Claims, No Drawings

PROCESS FOR PURIFYING MENTHOL

BACKGROUND OF THE INVENTION

1. Field of the Invention

The present invention relates to a process for purifying menthol and, more particularly, to a process for purifying menthol with high chemical purity and high optical purity by crystallization of crude menthol.

2. Description of the Related Art

Menthol, particularly (L)-menthol, is an important substance widely used in the field of, for example, flavors, fragrances and medicines since it gives cool taste and refreshing skin sensation. For example, (L)-menthol has conventionally been used as a flavor for food such as sweets or oral refreshments, for example, chewing gum or candy or for cigarettes or the like. However, presence of trace amounts of impurities (unnecessary optical isomer, etc.) can give detrimental influences on the quality thereof, and hence processes for purifying it has been investigated for a long time. Various processes have been known as purifying processes and, as one process, there is a process of purifying menthol by first converting it to its ester derivative, and then crystallizing it (see, patent document 1 described below). However, this process requires a step of converting menthol to the ester derivative thereof and a step of removing the protective group and, as a result, the number of necessary steps increases, thus not being industrially preferred.

In addition, processes for purification without converting to the ester or the like have also been known (see, patent documents 2 and 3 described below). For example, it has been reported in the patent document 2 that efficient optical resolution of the racemic form is possible under high pressure. In performing this process, however, a special apparatus is required. The patent document 3 describes a process wherein menthol or a mixture of menthol and water is brought into contact with supercritical carbon dioxide to thereby remove impure taste, chemical smell, etc. This process, however, requires an apparatus for generating supercritical carbon dioxide. Further, a recrystallization process of menthol from a solvent is also known. This recrystallization process is a comparatively simple process. However, since menthol has the comparatively low melting point (42° C.), the crystallization from a solvent must be carried out at low temperature. Such restrictions make it difficult to industrialize the process. In addition, this process has conventionally involved the problem that it is difficult to obtain highly pure (L)-menthol.

Patent document 1: U.S. Pat. No. 3,943,181
Patent document 2: JP-A-4-260401
Patent document 3: JP-A-9-217084

SUMMARY OF THE INVENTION

With the above-described circumstances in mind, the inventors have made various investigations on method for purifying menthol and, as a result, have found that using nitrile series solvent as a solvent when crystallizing menthol, menthol crystals are precipitated even at about room temperature and that the precipitated crystals are free of impurities including unnecessary optical isomer and optically and chemically substantially pure menthol crystals, thus pure menthol being able to be obtained with good yield. The invention has been made based on the above-described marvelous findings.

That is, the invention includes the following contents.

[1] A process for purifying menthol, which comprises dissolving crude menthol in nitrile series solvent, and then precipitate menthol by cooling the solution to thereby obtain optically substantially pure menthol.

[2] The process for purifying menthol as described in the item 1 above, wherein the nitrile series solvent is acetonitrile.

[3] The process for purifying menthol as described in the item 1 or 2 above, wherein menthol is (L)-menthol.

Additionally, the term "optically substantially pure" as used in the invention means an enantiomeric excess of about 99% e.e. (enantiomeric excess) or more which permits use thereof as flavors, fragrances or the like without further increasing the enantiomeric excess. Also, the term "chemically substantially pure" as used herein means a chemical purity of about 99% or more which permits use thereof as flavors, fragrances or the like without further increasing the chemical purity.

The enantiomeric excess is determined in the following manner.

That is, $$\text{enantiomeric excess} = (A-B) \div (A+B) \times 100$$

wherein A represents the content of an enantiomer existing in an excess amount, and B represents the content of the other enantiomer.

ADVANTAGEOUS EFFECT OF THE INVENTION

According to the invention, in purifying crude menthol, that is, optically active menthol containing one kind of isomer (e.g., L-isomer) in an excess amount, by crystallization, use of nitrile series solvent as a solvent for dissolving the crude menthol enables crystallization of menthol at a temperature of approximately room temperature without lowering the crystallization temperature to a degree which is industrially disadvantageous and, in addition, chemically and optically substantially pure menthol, preferably (L)-menthol, can be obtained. Thus, according to the invention, crude menthol can be purified to chemically and optically substantially pure menthol with ease and efficiency and under industrially advantageous conditions.

DETAILED DESCRIPTION OF THE INVENTION

The invention will be described in more detail below.

In the invention, crystallization of menthol is carried out in the following manner. First, crude menthol to be purified is mixed with nitrile series solvent to dissolve the crude menthol in the nitrile series solvent. Thereafter, the temperature of the solution of the crude menthol is lowered, and crystals precipitated are collected by filtration. Thus, optically substantially pure menthol can be obtained. The crystals collected by filtration may further be subjected, as needed, to additional purifying treatment such as distillation or sublimation. It suffices for the temperature for dissolving the crude menthol in the solvent to be a temperature equal to or lower than the melting point (42° C.) of menthol. For example, when the temperature for dissolving the crude menthol is set to about from 25 to about 40° C., the crystallization temperature can be set to from about room temperature (about 10° C. to abut 20° C.) to about a little lower temperature (about 0° C. to about 10) than the room temperature. Accordingly, it is preferred to dissolve the crude menthol by hot solvent to about the above-described temperature.

In the invention, the crude menthol to be used prior to purification by crystallization may be any crude menthol containing any optical isomers in an excess amount, and is not particularly limited. For example, the crude menthol may be natural menthol obtained by crystallizing an essential oil and centrifuging the product, a non-purified product obtained from a reaction mixture by isolating through such means as extraction, or a product obtained by further purifying the non-purified product by distillation, column chromatography or the like. The enantiomeric excess (hereinafter also referred to as "optical purity") is not particularly limited but, since a higher enantiomeric excess naturally leads to a higher crystallization yield, the enantiomeric excess of the crude menthol to be used is usually about 90% e.e. or more, preferably about 95% e.e. or more.

As a crystallization solvent in the invention, nitrile series solvents are used. Preferred examples of the nitrile series solvents are represented by the general formula of R—CN (wherein R represents an alkyl group). As more preferred solvents, there are illustrated those nitrile series solvents wherein R represents a lower alkyl group, for example, acetonitrile, propionitrile, butyronitrile, and isobutyronitrile. As the nitrile series solvents, acetonitrile is most preferred in the points of easy removability and inexpensive price. These nitrile series solvents may be used alone or may be used as a mixture with other solvent within the range wherein the objects of the invention can be attained. However, it is preferred to use nitrile series solvent alone. Examples of other solvents which can be used together with the nitrile series solvent include acetone and methyl acetate.

The amount of the solvent to be used may be an amount enough to dissolve menthol, and is from about 0.5 to about 10 times, preferably from about 1 to about 5 times, as much as the amount of menthol. In addition, the temperature for dissolution is preferably from 20 to 40° C., and the cooling temperature is preferably from 0 to 20° C. Cooling rate is not particularly limited, but gradual cooling is preferred. For example, it suffices to lower the temperature at a rate of from about 1 to about 5° C./minute by allowing the solution-containing vessel to stand at room temperature to thereby lower the temperature of the solution of menthol. In the case of cooling to a temperature equal to, or lower than, room temperature, cooling is carried out by properly employing cooling means. In this case, too, the temperature-decreasing rate may be the same as described hereinbefore.

Menthol obtained by the purification method of the invention gives strong cool feeling and gives refreshing and sharp taste. It can be used as such or, if necessary, after additional purifying treatment, as a flavor or fragrance component such as a component of peppermint, mint, a cooling sensation agent, a warming sensation agent or the like. Further, the menthol itself can be used in wide fields such as confectionery including chewing gum and candy, breath refreshers, oral refreshment products, bathing agents, cosmetics, tobaccos, medicines, etc., as is the same as before.

EXAMPLES

The invention will be specifically described hereinafter by reference to Examples which, however, do not limit the invention in any way.

Example 1

50 ml of acetonitrile was added to 16.3 g of crude menthol (chemical purity of (L)-menthol: 95%; optical purity: 97.3% e.e.), and the mixture was warmed to 30° C. to dissolve. This solution was cooled to 5° C., and crystals precipitated were collected by filtration and distilled to obtain 11.8 g (yield: 72%) of purified (L)-menthol. Chemical purity: >99%; optical purity: 99.6% e.e.

Example 2

54 g of crude menthol (content of (L)-menthol: 95.7%; optical purity: 97% e.e.; content of isomer of isomenthol: 2.5%; content of isomer of neoisomenthol: 1.8%; content of isomer of neomenthol: trace) was dissolved in 150 ml of acetonitrile at 30° C., and this solution was cooled to 5° C., followed by filtration to obtain 32 g of purified (L)-menthol. GC (gas chromatography) analysis revealed that no isomers (isomenthol, neoisomenthol, and neomenthol) were detected with the purified (L)-menthol.

Comparative Example 1

20 ml of acetone was added to 80 g of crude menthol (chemical purity of (L)-menthol: 95%; optical purity: 97.3% e.e.) and the crude menthol was dissolved at room temperature. This solution was cooled to 0° C. However, no crystals were precipitated.

Comparative Example 2

10 ml of isopropyl ether was added to 10 g of crude menthol (chemical purity of (L)-menthol: 95%; optical purity: 97% e.e.) and the crude menthol was dissolved at room temperature. This solution was cooled to −25° C. to conduct crystallization. Purities of the precipitated crystals were measured to find that chemical purity was 95% and optical purity was 97%, which are the same as those of the crude menthol and are unchanged.

Comparative Example 3

100 ml of ethanol was added to 100 g of crude menthol (chemical purity of (L)-menthol: 95%; optical purity: 97% e.e.), and the crude menthol was dissolved at room temperature. This solution was cooled to −20° C., but no crystals were precipitated.

What is claimed is:

1. A process for purifying menthol, which comprises dissolving crude menthol in nitrile series solvent and then precipitate menthol by cooling the solution to thereby obtain optically substantially pure menthol.

2. The process for purifying menthol according to claim 1, wherein the nitrile series solvent is acetonitrile.

3. The process for purifying menthol according to claim 1 or 2, wherein menthol is (L)-menthol.

* * * * *